United States Patent [19]
Mehdizadeh

[11] Patent Number: 4,932,395
[45] Date of Patent: Jun. 12, 1990

[54] HEMI-LAMINECTOMY RETRACTOR ATTACHMENT DEVICE

[76] Inventor: Hamid M. Mehdizadeh, 2505 Samaritan Dr., Ste. 502, San Jose, Calif. 95124

[21] Appl. No.: 195,261
[22] Filed: May 18, 1988
[51] Int. Cl.$^5$ .................... A61B 17/02
[52] U.S. Cl. .................... 128/20
[58] Field of Search .................... 128/20, 3, 339, 355; 24/598

[56] References Cited

U.S. PATENT DOCUMENTS

| | | | |
|---|---|---|---|
| 2,450,194 | 9/1948 | Glaser | 128/20 |
| 2,591,063 | 4/1952 | Goldberg | 128/339 |
| 2,701,562 | 2/1955 | Michael | 128/20 |
| 3,542,015 | 11/1970 | Steinman | 128/20 |
| 3,762,401 | 10/1973 | Tupper | 128/20 |
| 3,762,418 | 10/1973 | Wasson | 128/339 |
| 3,823,709 | 7/1974 | McGuire | 128/20 |
| 4,034,746 | 7/1977 | Williams | 128/20 |
| 4,274,398 | 6/1981 | Scott, Jr. | 128/20 |
| 4,430,991 | 2/1984 | Darnell | 128/20 |

FOREIGN PATENT DOCUMENTS

| | | | |
|---|---|---|---|
| 366103 | 3/1922 | Fed. Rep. of Germany | 128/20 |
| 3234875 | 3/1984 | Fed. Rep. of Germany | 128/20 |
| 1319834 | 6/1987 | U.S.S.R. | 128/20 |

*Primary Examiner*—Edward M. Coven
*Assistant Examiner*—Mark S. Graham
*Attorney, Agent, or Firm*—Rosenblum, Parish & Bacigalupi

[57] ABSTRACT

A hemi-laminectomy retractor attachment device adapted for use with prior art retractors. In a preferred embodiment the device includes two hook-shaped members that are joined together by a length of strong, flexible cord. The hook-shaped members are narrow enough to fit between spinal bones to brace against the spinal ligaments, and the cord is engaged with the retractor arm.

3 Claims, 3 Drawing Sheets

56
12
32
10
14
54
58
52
54
42
44
46
40
48
50

FIG.1
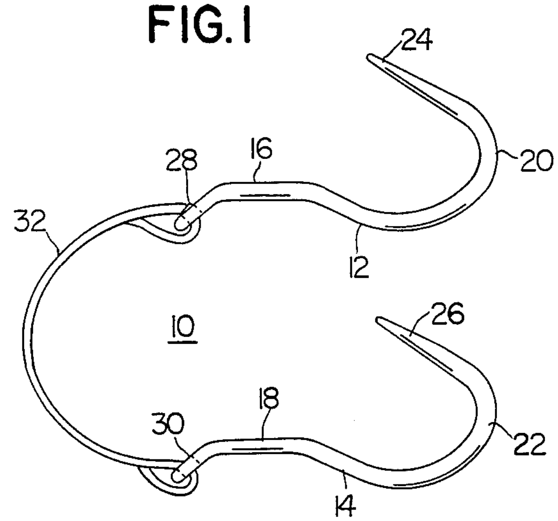
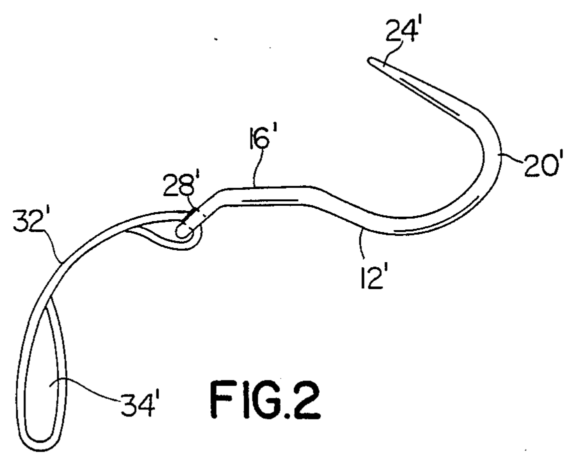
FIG.2

HEMI-LAMINECTOMY RETRACTOR ATTACHMENT DEVICE

BACKGROUND OF THE INVENTION

1. Field of the Invention

The present invention relates to surgical retractors and more particularly to an attachment that is particularly suited for use in hemi-laminectomy surgical procedures.

2. Description of the Prior Art

Retractors that are utilized in laminectomy and hemi-laminectomy surgery are formed with blade-like attachments for gripping and manipulating spinal muscles. Such blades typically have a plurality of prongs or smooth surfaces to pull muscles to one side or hold muscles in an appropriate place to facilitate the gripping of the muscle.

In performing a hemi-laminectomy procedure, one blade of a retractor grips the spinal muscle in the typical manner. The other blade is preferably adapted to fit between two adjacent spinal bone elements and engage a spinal tendon that resides next to the bone elements. It is often the case that insufficient spacing exists between the adjacent bone elements to permit the hemi-laminectomy device to pass therebetween. This situation occurs because the prior art hemi-laminectomy attachments are relatively thick in diameter and the patient's spinal column spacing may be insufficient due to age or deterioration. Such relatively thick retractor elements also may obstruct visualization of the exposed area. A relatively thick retractor element is necessary in the prior art configurations due to the requirement for significant bending strength in order for the device to perform properly.

Applicant is aware of several U.S. patents for retractors. Williams U.S. Pat. No. 4,034,746 teaches a scissor-like retractor having a blade member and a rod-like member that are utilized to open an incision for surgical procedures. Another relevant retractor is depicted in U.S. Pat. No. 2,450,194. U.S. Pat. Nos. 4,430,911 to Darnell, 4,274,398 to Scott, Jr., 3,823,709 to McGuire, and 3,762,401 to Tupper all teach other types of surgical retractors, the relevant features of these patents being the utilization of hook-shaped tissue-holding members that are utilized to hold an incision open for surgical procedures. However, none of the prior art devices and patents known to Applicant contain all of the features of Applicant's invention, which are particularly suited for hemi-laminectomy surgical procedures.

There is therefore a need for a hemi-laminectomy retractor attachment which easily fits between minimally-spaced spinal bone elements, yet is strong enough to withstand pressure while fitting a wide range of sizes and shapes of spinal areas.

SUMMARY OF THE INVENTION

It is an object of the hemi-laminectomy attachment device of the present invention to provide a device having a minimal thickness such that it will easily pass between the bony elements of a patient's spinal process and elements.

It is another object of the hemi-laminectomy attachment device of the present invention to provide a device which is strong enough to give and produce a better visualization of the operated area such that a surgeon can perform his/her surgery in a wide and more open space.

It is a further object of the hemi-laminectomy attachment device of the present invention to provide a device that is adapted for use with most currently available laminectomy retractors.

It is yet another object of the hemi-laminectomy retractor attachment device of the present invention to provide a device that is inexpensive and easy to use.

The hemi-laminectomy attachment device of the present invention includes one or two hook-shaped members. Each hook-shaped member is formed with an eye at the shank end for attachment to a length of strong, flexible cable. In the two hook-shaped member embodiment the two hook-shaped members are joined together by a single length of cable. The diameter of the shank of each hook is sufficiently small to allow it to pass through narrow spaces between spinal bone elements, yet the strength of each hook-shaped member is sufficient to withstand bending pressure.

It is an advantage of the hemi-laminectomy attachment device of the present invention that it provides a device having a minimal thickness such that it will easily pass between the bony elements of a patient's spinal process and elements.

It is another advantage of the hemi-laminectomy attachment device of the present invention that it provides a device which is strong enough to give and produce a better visualization cf the operated area such that a surgeon can perform his/her surgery in a wide and more open space.

It is a further advantage of the hemi-laminectomy attachment device of the present invention that it provides a device that is adapted for use with most currently available laminectomy retractors.

It is yet another advantage of the hemi-laminectomy retractor attachment device of the present invention that it provides a device that is inexpensive and easy to use.

The foregoing and other objects, features, and advantages of the present invention will be apparent from the following detailed description of the preferred embodiments which make reference to the several figures of the drawing.

IN THE DRAWING

FIG. 1 is a pan view of the hemi-laminectomy retractor attachment device of the present invention;

FIG. 2 is a plan view of an alternative embodiment of the hemi-laminectomy retractor device of the present invention;

DESCRIPTION OF THE PREFERRED EMBODIMENTS

Figure 3:
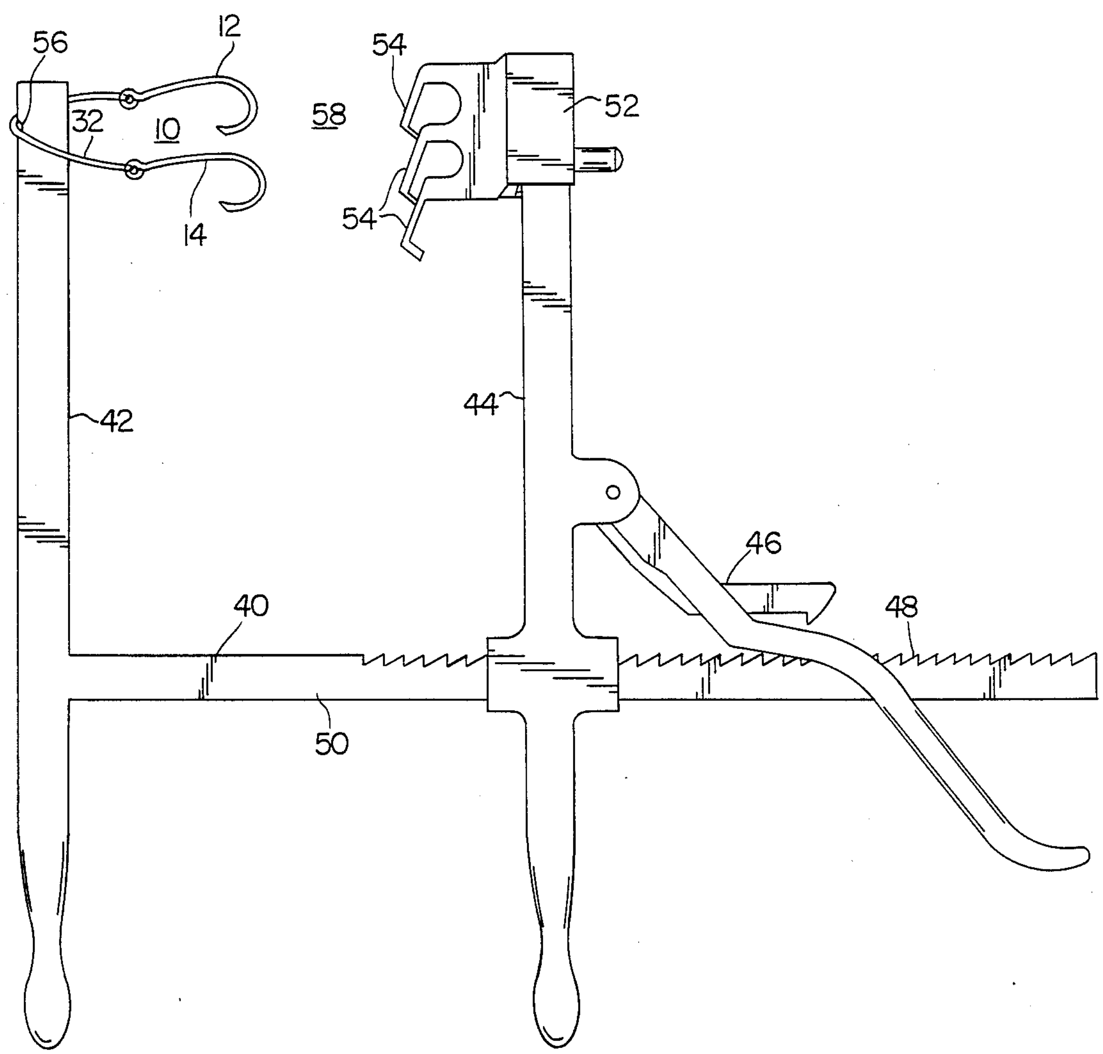
FIG. 3 is a pan view of the hemi-laminectomy retractor attachment device depicted in FIG. 1 shown in an attached orientation with a prior art laminectomy retractor.

As depicted in FIG. 1, a preferred embodiment of the hemi-laminectomy retractor attachment device 10 of the present invention includes two hook-shaped members 12 and 14. Each hook-shaped member 12 and 14 is formed with a shank portion 16 and 18 respectively, a curved portion 20 and 22 respectively having an arc of approximately 180 degrees, and a tip portion 24 and 26 respectively. The distal end of the shank portion 16 and 18 respectively is formed with an eye 28 and 30 respectively. A strong, flexible cord 32 is utilized to join the two hook-shaped members 12 and 14 together by passing a first end of the cord 32 through eye 28 and the other end of the cord through eye 30. The ends of the cord are looped and engaged to the cord 32. The cord 32 may be formed from such materials as a length of wire, braided wire, chain or other material that is sufficiently strong yet flexible.

The size of the hook-shaped members 12 and 14 may be varied according to the operational requirements. Thus, the radius of curvature of the curved portions 20 and 22 as well as the length of the shank portions 16 and 18 and the length of the tip portions 24 and 26 may be varied to suit particular operational situations. Likewise, the length of the cord 32 may be altered to suit particular needs. In the preferred embodiment the radius of curvature of the curved portion 20 or 22 may vary according to the particular application but is approximately 1 centimeter, the length of the shank portion 16 and 18 is approximately 3 centimeters, the diameter of the shank portion may also vary but is approximately 2 millimeters, the length of the tip portion 24 and 26 is approximately 1.5 centimeters, and the length of the cable 32 is approximately 8 centimeters. The preferred material for members 12 and 14 is stainless steel, and the cable 32 is formed from braided stainless steel wire which can be lengthened or shortened to fit one or several hemi-laminectomy areas. The cable also may be changed to any other material providing it will be strong and not tear during surgery.

FIG. 2 depicts an alternative embodiment of the present invention comprising a single hook-shaped member 12'. As will appear from a comparison of FIGS. 1 and 2, corresponding portions of hook-shaped member 12' are identified utilizing primed numbers corresponding to the numbering of FIG. 1. (able 32' of the hook-shaped member 12' of FIG. 2 is formed with a relatively large loop 34'. The dimensions of the preferred embodiment of the hook-shaped member 12' are substantially similar to those of the hook-shaped member 12 of FIG. 1. The length of the cable 32' is approximately 4 centimeters and the diameter of loop 34' is approximately 2.5 centimeters.

FIG. 3 depicts the present invention of FIG. 1 as utilized with a prior art laminectomy retractor 40 that is more fully described in U.S. Pat. No. 2,450,194. The retractor 40 is formed with two arms 42 and 44 that are moveable relative to each other through the utilization of a ratchet mechanism 46 which engages a plurality of teeth 48 formed on a ratchet bar 50 that is fixedly engaged to arm 42. It will therefore be appreciated that arm 44 is slidably engaged to bar 50 and that the operation of ratchet 46 within the various teeth 48 of bar 50 will cause arm 44 to move laterally with respect to arm 42.

As depicted in FIG. 3, a blade 52 having three prongs 54 is engaged to the distal end of the moveable arm 44. The hemi-laminectomy attachment device 10 of FIG. 1 of the present invention is engaged to the fixed retractor arm 42. This engagement is accomplished through the looping of the cable 32 around the arm 42, such that the hook-shaped members 12 and 14 are disposed toward the blade 52. A notch 56 may be formed in the distal end of arm 42, such that the cable 32 will reside in said notch, whereby the cable 32 will be inhibited from sliding off of the distal end of arm 42 when the device is utilized. It will therefore be appreciated that upon the operation of ratchet 46 that arm 44 with its attached blade 52 will move laterally with respect to the fixed orientation of the hook-shaped members 12 and 14; that is, that the gap 58 between the prongs 54 and the hook-shaped members 12 and 14 is adjusted through use of the ratchet mechanism 46.

The alternative embodiment of the present invention depicted in FIG. 2 is also formed for engagement with the arm 42 of the laminectomy retractor 40 depicted in FIG. 3. The engagement is achieved by sliding the loop 34' over the projecting end of arm 42. If a notch 56 is provided in arm 42, the loop 34' would reside within the notch 56.

Figure 4:
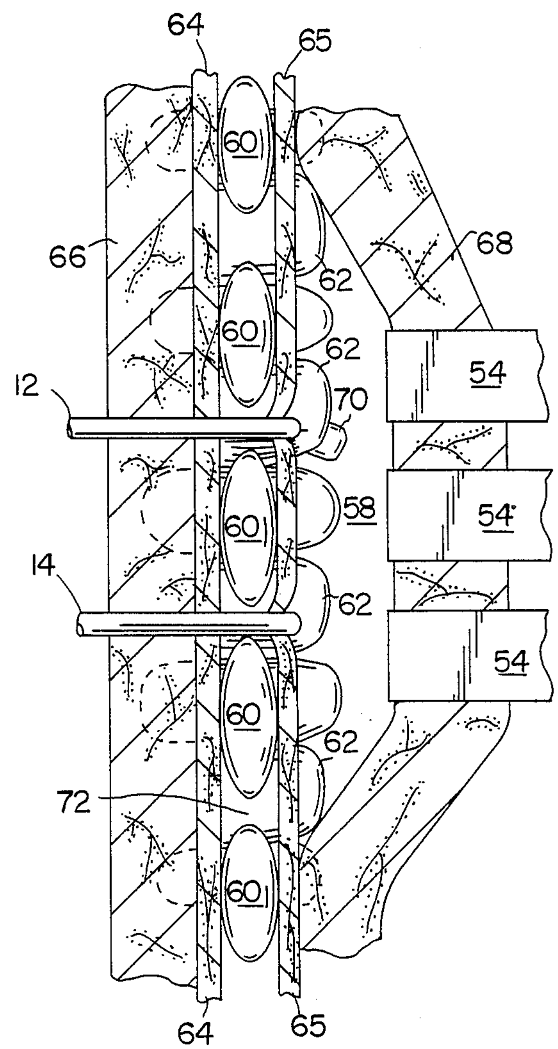
FIG. 4 is a simplified plan view of a hemi-laminectomy operation procedure showing the utilization of the present invention.

FIG. 4 depict: a simplified drawing of a hemi-laminectomy operation utilizing the present invention depicted in FIG. 1. Five bony elements 60 of the spinal column are shown separated by spinal discs 62. Two spinal muscles and tendons 64 and 65 are disposed parallel to the spinal column immediately next to the bony elements 60 thereof. The left side muscle sheath 66 is shown in its undisturbed position, whereas the right side muscle sheath 68 is shown pulled away by the prongs 54 of the blade 52 of a hemi-laminectomy retractor, such as that depicted in FIG. 3. A damaged portion 70 of a spinal disc 62 is revealed for surgical procedure. The two hook-shaped members 12 and 14 of the present invention are shown in position braced against the right side spinal tendon 65, each hook-shaped member 12 and 14 having passed between the protruding bony elements 60 of the spinal column. Because the tendon 65 is more firmly attached to the spinal column elements 60, the muscle sheath 68 is moved laterally by the widening of the gap 58 between the hook-shaped members 12 and 14 and the prongs 54 through the operation of the ratchet 46 of the retractor 40.

As shown in FIG. 4, it is to be appreciated that hook-shaped members 12 and 14 possess a sufficiently narrow diameter that they may be inserted between the spaces between the bony elements 60 to engage the spinal tendon 65. In many instances, such as with young patients or elderly patients or patients with differing growth patterns, the spaces between the spinal bony elements 60 may be quite narrow, such that prior art hemi-laminectomy devices will not fit through the narrow spaces between the bony elements. The prior art devices tend to be thicker in diameter because they are configured to withstand bending forces. The shanks 16 and 18 of the hook-shaped members experience mainly tension forces and, owing to the nature of the material (stainless steel in the preferred embodiment), can be smaller in diameter.

It is also to be realized that the device 10 is quite versatile in its applications. That is, the hook-shaped members need not be placed within two sequential gaps between bony members 60 as is depicted in FIG. 4. Specifically, hook-shaped member 14 could be disposed in gap 72 as identified in FIG. 4. Also, more than one of the devices 10 could be disposed upon a single retractor arm 42, whereby three or four hook-shaped members would be available for insertion between various of the bony elements 60 of the spinal column. Additionally, the multiple hook-shaped members need not be of the same size for some particular applications.

While the invention has been particularly shown and described with reference to certain preferred embodiments, it will be understood by those skilled in the art that various alterations and modifications in form and detail may be made therein. Accordingly, it is intended that the following claims cover all such alterations and modifications as may fall within the true spirit and scope of the invention.

What I claim is:

1. A hemi-laminectomy retractor attachment device adapted for utilization with laminectomy retractors having a first structural member and a second structural member, wherein said structural members are capable of lateral movement relative to each other, said attachment device comprising:

a first tissue-engaging member, being formed in a substantially hook-shaped configuration, having a first shank portion having a length of approximately three centimeters that is integrally joined to a first curved portion having an arc of approximately 180 degrees and a radius of curvature of approximately one centimeter, said first curved portion terminating in a first tip portion having a length of approximately one and one-half centimeters, and said first shank portion being formed with a means to engage a joining member at the end thereof distal to said first curved portion;

a second tissue-engaging member, being formed in a substantially hook-shaped configuration, having a second shank portion that is integrally joined to a second curved portion having an arc of approximately 180 degrees, said second curved portion terminating in a second tip portion, and said second shank portion being formed with a means to engage a joining member at the end thereof distal to said second curved portion;

a joining member having a first end and a second end, said first end being engaged to said first tissue-engaging member and said second end being engaged to said second tissue-engaging member, said joining member being adapted for engagement with said first structural member of said laminectomy retractor.

2. A device as described in claim 1 wherein said second tissue-engaging member is formed with said second shank portion having a length of approximately three centimeters, said second curved portions having a radius of curvature of approximately one centimeter, and said second tip portion having a length of approximately one and one-half centimeters.

3. A hemi-laminectomy retractor attachment device adapted for utilization with laminectomy retractors having a first structural member and a second structural member, wherein said structural members are capable of lateral movement relative to each other, said attachment device comprising:

a first tissue-engaging member, being formed in a substantially hook-shaped configuration, having a first relatively straight shank portion that is integrally joined to a first curved portion having an arc of approximately 180 degrees, said first curved portion terminating in a first relatively straight tip portion, and said first shank portion being formed with a closed loop portion at the end thereof distal to said first curved portion;

a second tissue-engaging member, being formed in a substantially hook-shaped configuration, having a second relatively straight shank portion that is integrally joined to a second curved portion having an arc of approximately 180 degrees, said second curved portion terminating in a second relatively straight tip portion, and said second shank portion being formed with a closed loop portion at the end thereof distal to said second curved portion;

a joining member being formed substantially as a flexible cord, having a first end and a second end, said first end being engaged to said first tissue-engaging member at said loop portion thereof and said second end being engaged to said second tissue-engaging member at said loop portion thereof, said joining member being adapted for engagement with said first structural member of said laminectomy retractor;

said first tissue-engaging member being formed from stainless steel, said first shank portion having a diameter of approximately 2 millimeters and a length approximately three centimeters, said first curved portion having a radius of curvature of approximately one centimeter, and said first tip portion having a length of approximately one and one-half centimeters;

said second tissue-engaging member being formed from stainless steel, said second shank portion having a diameter of approximately 2 millimeters and a length of approximately three centimeters, said second curved portion having a radius of curvature of approximately one centimeter, and said second tip portion having a length of approximately one and one-half centimeters;

and wherein said joining member is formed from braided stainless steel wire having a length of approximately eight centimeters.

* * * * *